United States Patent [19]

Lüssi

[11] Patent Number: 5,535,141
[45] Date of Patent: Jul. 9, 1996

[54] AUTOCLAVE

[75] Inventor: André Lüssi, Wabern, Switzerland

[73] Assignee: Sintra Holding AG, Sursee, Switzerland

[21] Appl. No.: 257,549

[22] Filed: Jun. 9, 1994

[30] Foreign Application Priority Data

Jun. 15, 1993 [EP] European Pat. Off. ............. 93810429

[51] Int. Cl.$^6$ .................................................. G05B 19/00
[52] U.S. Cl. ............................ 364/550; 364/140; 422/119
[58] Field of Search ............................ 235/375; 364/140, 364/146, 189, 550; 422/119

[56] References Cited

U.S. PATENT DOCUMENTS

| | | | |
|---|---|---|---|
| 3,827,030 | 7/1974 | Seipp | 364/147 X |
| 4,261,950 | 4/1981 | Bainbridge et al. | 422/116 X |
| 4,319,319 | 3/1982 | Wygant | 364/143 |
| 4,728,949 | 3/1988 | Platte et al. | 340/825.37 |
| 4,785,417 | 11/1988 | Obrea | 364/550 X |
| 4,792,996 | 12/1988 | Oyama | 364/192 X |
| 4,812,994 | 3/1989 | Taylor et al. | 364/464.02 |
| 4,837,764 | 6/1989 | Russello | 371/16.1 |
| 4,862,872 | 9/1989 | Yabe et al. | 600/133 |
| 5,124,926 | 6/1992 | Barns-Slavin et al. | 364/464.03 |
| 5,128,857 | 7/1992 | Okada et al. | 364/140 |
| 5,270,948 | 12/1993 | Obrien et al. | 364/550 |

FOREIGN PATENT DOCUMENTS 9203170 3/1992 European Pat. Off. .

OTHER PUBLICATIONS

Patent Abstracts of Japan JP60024639.
Tylkowski et al: "Progammierbare Dampfsterilisatoren" Medizintechnik, Bd. 27 No. 3 Sep. 1987; pp. 67–80.

*Primary Examiner*—Edward R. Cosimano
*Attorney, Agent, or Firm*—Pearne, Gordon, McCoy & Granger

[57] ABSTRACT

The autoclave includes a sterilization chamber (2) to receive articles to be sterilized, which are used in medical treatment. With a door (1) the sterilization chamber (2) can be locked shut. Placed on top is a control unit (6) including a control panel (9) with control elements (10) and a card reader (11). Disposed above the control panel is an indicator panel (12) for displaying in particular device data and for guiding the user by means of an LCD. Using chip cards, which have an electronic component with a non-volatile memory, and which can be electrically connected to the card reader permitting data exchange with the control unit, special sterilization programs can be run, the authorization to use the autoclave can be checked, and further functions, such as blocking or enabling individual control elements, can be executed.

9 Claims, 4 Drawing Sheets

AUTOCLAVE

BACKGROUND OF THE INVENTION

The present invention concerns an autoclave, especially for articles which are used in medical treatment, with a sterilization chamber which can be locked with a door, a control unit to control and monitor various sterilization programs, with operating elements to input control signals to the control unit, as well as an indicator panel to guide the user and to display status information.

All microorganisms capable of reproduction, including their especially resistant spores, are killed through sterilization. This also applies to microorganisums which are not pathogens, but which could endanger weakened patients, e.g. through pyrogenic, i.e. febrifacient metabolic products. Viruses are inactivated irreversibly.

Thus articles used in medical treatment are sterilized when a patient's natural resistance to microorganisms is impaired. This would apply, for example, in the case of open wounds (operations following accidents, etc.), inside body cavities and mucous membranes (endoscopy), where there is unprotected layers of tissue (as a result of burns), as well as in the case of changed immunological reactions (following transplantations).

Autoclaves are made especially to sterilize articles which were previously packaged in special paper or in special plastic.

With the frequently used steam sterilization, saturated steam, which penetrates the packaging material, condenses on the articles to be sterilized. The condensation heat heats these articles up. Hot condensate penetrates the cell membranes of the microorganisms and attacks the nuclei directly. Saturated steam sterilizes very reliably despite relatively low sterilization temperature and short reaction time. Steam does not leave behind any poisonous residue on the sterilized objects.

Use of steam sterilization is preferred for textiles of cotton or heat-resistant mixed fabrics, for metal objects with sufficient corrosion resistance and for many articles of rubber, plastic, ceramic or glass. The sterilization temperature in these cases is usually 134 degrees. Cellulose, liquids, delicate rubber goods, plastic parts, also articles of glass and delicate mechanical devices are sterilized at a reduced temperature of 120 degrees.

It is important to consider the fact that the articles to be sterilized with saturated steam must remain stable when exposed to rising temperature, moisture, and the unavoidable changes in pressure and temperature. Organic materials are not suitable for sterilization in steam.

During the condensation of the saturated steam, air and other non-condensable gases are discharged on, or in, the object to be sterilized. The removal of these gases prior to sterilization and the drying of the sterilized object are the most important tasks of steam sterilization technology.

The object to be sterilized plays an important role in the sterilization process. The sterilization process depends upon the heat absorption of this object, thus upon its rise in temperature, its weight and its specific heat as well as its impedance, which prevents a free flowing off of the air. Instruments and special articles are more difficult to sterilize than textiles. Consequently various sterilization processes have proved suitable for various types or classes of objects to be sterilized which have then been incorporated into a preferably applied sterilization program for the corresponding class.

An autoclave generally comprises a sterilization chamber which can be locked with a door, the chamber, thermally insulated, being preferably of double-shell design. A blast of steam under pressure can be introduced into the sterilization chamber whereby a hot, humid climate with a certain temperature and with a certain excess pressure can build up. By means of a vacuum pump, the pressure in the sterilization chamber can likewise be reduced for certain sterilization phases. Installed in the sterilization chamber to measure the temperature and the absolute pressure are at least a thermometer and a manometer. A control unit serves to control and monitor the individual steps or sterilization phases during the course of a program. By means of operating elements, individual sterilization programs can be selected and started for particular articles to be sterilized. Important data such as the temperature and the pressure in the sterilization chamber are displayed on an indicator panel. The autoclave is usually surrounded by a casing, preferably of chrome nickel steel.

A sterilization process runs in such a way that, depending upon the object to be sterilized, a vacuum is formed at least once for at least a short time prior to the actual sterilization in which hot steam under a pressure of about 2 to 4 bar and at a temperature of 120 degrees to about 140 degrees is present in the sterilization chamber for roughly 1 to 30 minutes. A fractionated vacuum process can be applied in which, by introducing blasts of steam, following the building up of a vacuum, the vacuum disintegrates and is finally formed again. This cycle of build-up and disintegration can take place a few times, preferably about three times. In this way air bubbles present in inaccessible places on the objects to be sterilized can be reliably removed before the actual sterilization. Following sterilization another vacuum is formed in the sterilization chamber and is maintained for some minutes. This vacuum serves to dry the sterile objects. The drying process can likewise be carried out with a fractionated vacuum process.

That flawlessly sterile articles are used can be vital for patients. Operation of the autoclave thus requires the the greatest care and is not to be done by just anyone. To prevent just anyone from operating the appliance and to have perfect controls on the personnel authorized to operate it, and to make sterilization programs more flexible, improvements in autoclaves have been sought.

SUMMARY OF THE INVENTION

An improved autoclave in the above sense is characterized in that the control unit has a computing means and a memory means, in that a read-write device and several data carrier elements are provided, each data carrier element being equipped with a non-volatile further memory means and being connectible to the read-write device in a way to permit data exchange.

To increase the possibilities of input or output, respectively, of commands or signals, respectively, to or from the control unit of the autoclave, respectively, the control unit has been equipped with a read-write device, preferably a card reader. By means of data carrier elements or so-called chip cards, on which information can be stored and called up again, and of which an unlimited number can be made available, a large number of additional functions and/or monitoring tasks can be undertaken on the autoclave without detracting from the simplicity of operation, as would be the case if, instead of the card reader, the operation would have to be carried out with additional operating elements which would be disposed on the control panel. Despite the many multifunctions, which can be realized with the chip cards and with the card reader, operation of the autoclave is not made more difficult, but rather simplified.

The chip cards can be divided up into several categories, different data being stored in their memory means, depending upon the category. A distinction can be made, for example, between so-called operating personnel cards and executive cards. In the second case, using a corresponding identification code stored in the memory means of the corresponding executive card which is recognized by the control unit of the autoclave, it could be arranged that the owner of this executive card would be able to change individual functions on the autoclave, such as, for example, individual operating elements, which are intended to select sterilization programs, to block or enable or establish that only operating personnel with chip cards having very particular operator identifications are authorized to operate the autoclave. With an executive card furthermore it can be determined at any time which operators are authorized to operate the corresponding sterilization appliance. For the authorized operators, an assigned identification code or an authorization number could be displayed, for example on an LCD provided on an indicator panel. This information could also be given out on a printer which could be connected to the autoclave or on a printer built into the autoclave.

In the first case, with the chip cards foreseen for the operating personnel, it could be arranged that the operating elements for the autoclave are activated only if, following insertion of the chip card assigned to the corresponding person, the authorization of that person is established on the basis of an identification code present both in the memory means on the chip card and in the memory means of the control unit. In this way unauthorized persons can be prevented from carrying out inappropriate sterilization processes.

It is likewise possible to have special sterilization programs contained on one of the chip cards. Following insertion of such a chip card into the card reader, the control unit would recognize, on the basis of another identification code, that a special sterilization program has been stored on the chip card which should now be carried out. The program data are loaded in the control unit, and the individual sterilization phases are processed according to this special program.

Using so-called chip cards for data security, the configuration stored in the memory means of the control unit, or respectively the initialization data established therein for the autoclave, can be copied into the memory means of these chip cards. In the event of a possible breakdown of the autoclave, the appliance would not have to be configured or initialized again by means of tedious, detailed work, but instead all data previously stored in the memory means of the control unit can be loaded again into this memory means using the chip card for data security. These data could also include the various authorization codes and/or identification codes.

BRIEF DESCRIPTION OF THE DRAWINGS

With the aid of a preferred embodiment, the invention will be described more closely in the following with reference to the drawing in which.

DETAILED DESCRIPTION OF THE PREFERRED EMBODIMENT

Figure 1:
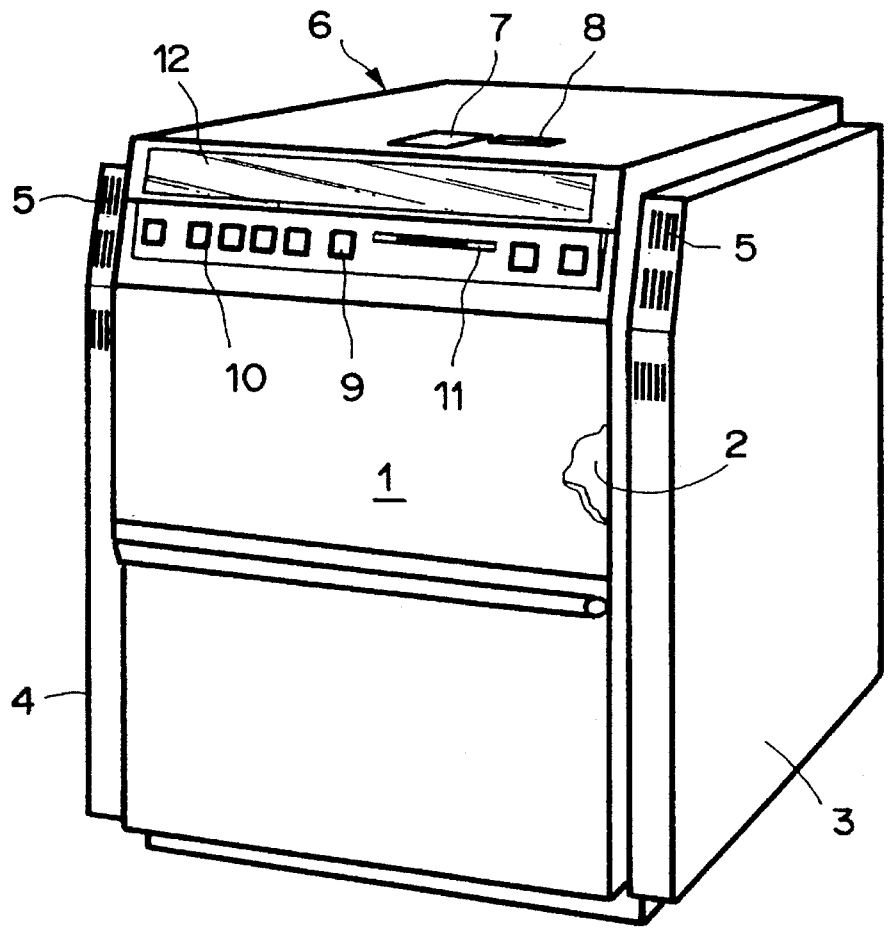
FIG. 1 is an exterior view of a table-top autoclave.

The autoclave shown as an example in FIG. 1 is a table-top sterilizer which works with the same sterilization process as the large units. The appliance is foreseen for use in medical and dental practices, hospitals and generally in all areas where surgical treatments can be carried out.

The autoclave comprises a door 1, operated by hand, which is designed as a sliding door opening vertically downward. By means of the door, a sterilization chamber 2 can be opened up into which the articles to be sterilized are introduced. The door is provided with safety locking, which makes it impossible to start up the autoclave before the door is shut and locked or to open the door before a running sterilization program has been completed. For reasons of thermal insulation, the sterilization chamber 2 itself is surrounded by a double casing. The entire appliance is built into a shell of stainless steel. Reference numeral 5 indicates cooling apertures in the two side walls 3 and 4 which are intended to maintain an air convection cooling. A control unit 6 is placed on top of the autoclave. A built-in ventilator 7 serves, together with the cooling apertures 5, to cool the components built into the control unit to an optimal operating temperature.

Designated 8 is a printer output which can emit paper printed by a built-in wire matrix printer. The individual sterilization phases of each sterilization program are printed out at the end of the program. The printed record is cut off and expelled from the printer output. Error messages are printed in red type immediately as they arise. They are visible on the printed record at the end of the program.

Disposed on the front side of the control unit 6 is a control panel 9, comprising several operating elements 10 which will be gone into later, as well as a read-write device, a card reader 11. Designated 12 is an indicator panel disposed above the control panel.

Figure 2:
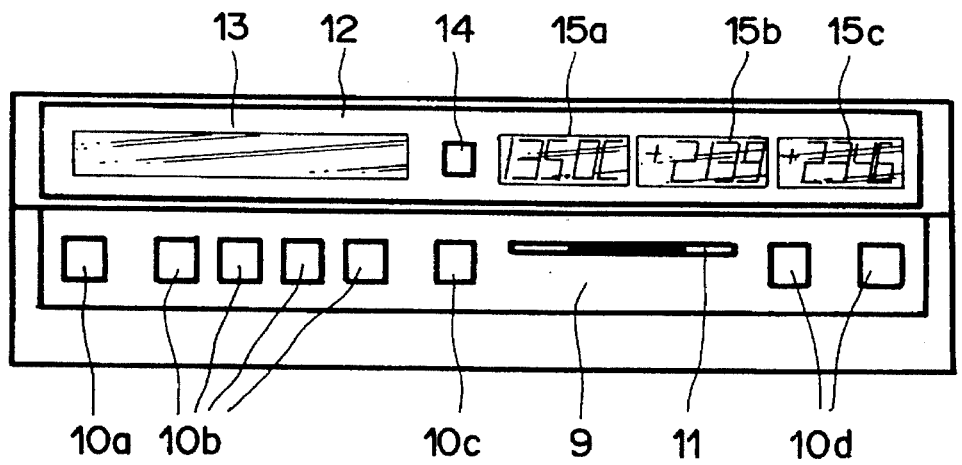
FIG. 2 shows, in an enlarged front view, the control panel and the indicator panel of the autoclave according to FIG. 1.

The control panel 9 and the indicator panel 12 are presented enlarged in a front view in FIG. 2. Disposed on control panel 9 from left to right are an on/off button 10a, four program selection buttons 10b, a shift button 10c, the previously mentioned card reader 11 and two control buttons 10d. Provided on indicator panel 12 is, on the left, an LCD 13, especially to guide the user and to display the sterilization program phases in plain text. Designated 14 is a control light which remains lit as long as excess pressure prevails in the sterilization chamber. Further indicators are designated by 15a–15c, which are seven-segment displays. At 15a the temperature in the sterilization chamber is displayed in degrees Celsius, at 15b the pressure of the sterilization chamber in bar, and at 15c the pressure in the steam generator, likewise in bar.

Figure 3:
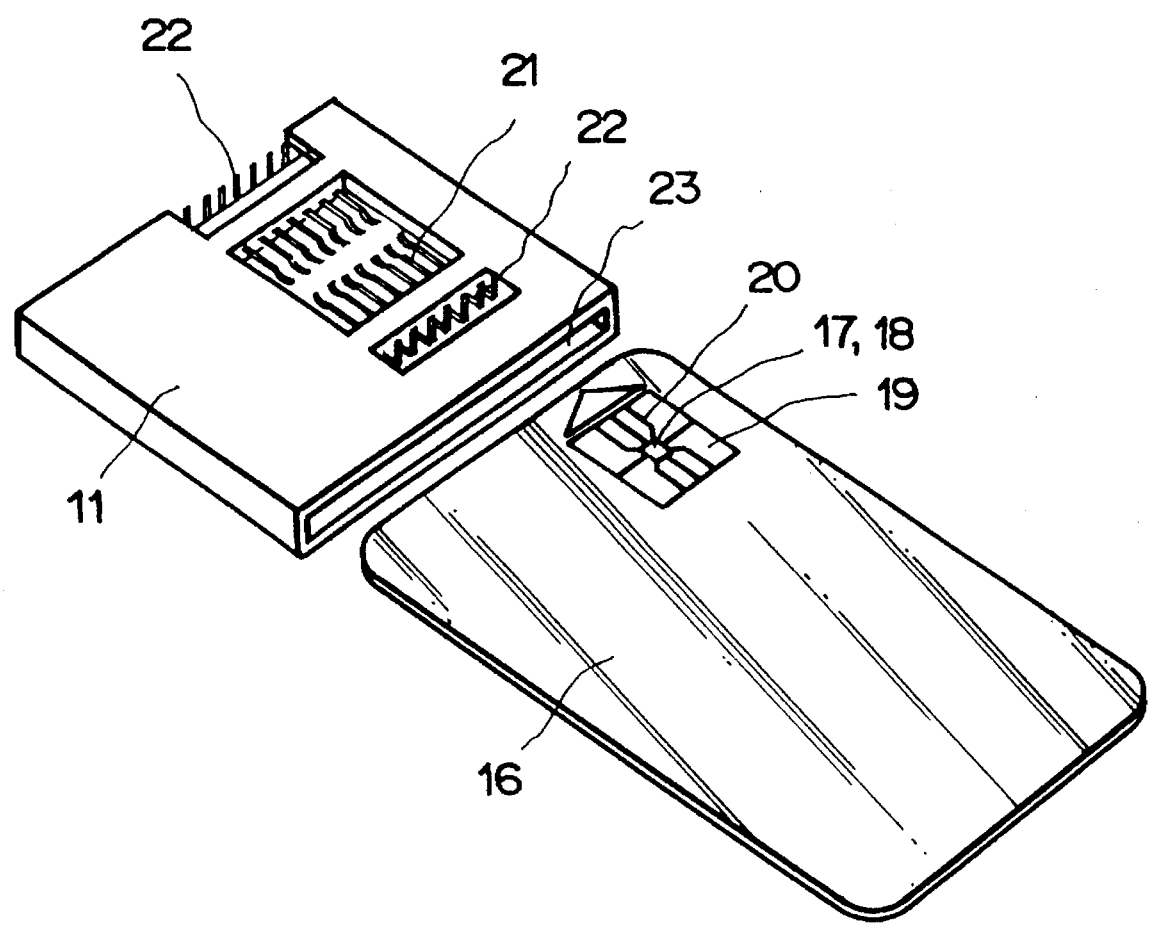
FIG. 3 shows a card reader with a chip card.

Presented in FIG. 3 are the card reader 11 and a chip card 16. An insertion slot 23 of the card reader 11 is turned toward the chip card 16 shown lying next to the card reader. Disposed on chip card 16 is an electronic component 17, which has at least one memory means 18. The memory means is usually designed as an EEPROM. This is a non-volatile semiconductor memory, which can be written on and erased electrically. Contained in card reader 11 are sensing contacts 21, essentially in two rows, which lead to contacts 22, which are likewise disposed in two rows. From contacts 22, the card reader is connected to the control electronics via a connecting cable.

The electronic component 17 on the chip card 16 is covered by a metallized contact surface 19. This surface is divided up into partial surfaces by individual insulation areas 20 in such a way that, with the chip card 16 inserted into the insertion slot 23 of card reader 11, one sensing contact 21 each is associated with one partial surface each. A sensing process is enabled only when an end position contact in the card reader (not shown in the figures) reports the complete insertion of the chip card. Each of the metallized partial surfaces is connected to a contact of the electronic component 17 disposed on the chip card 16.

Figure 4:
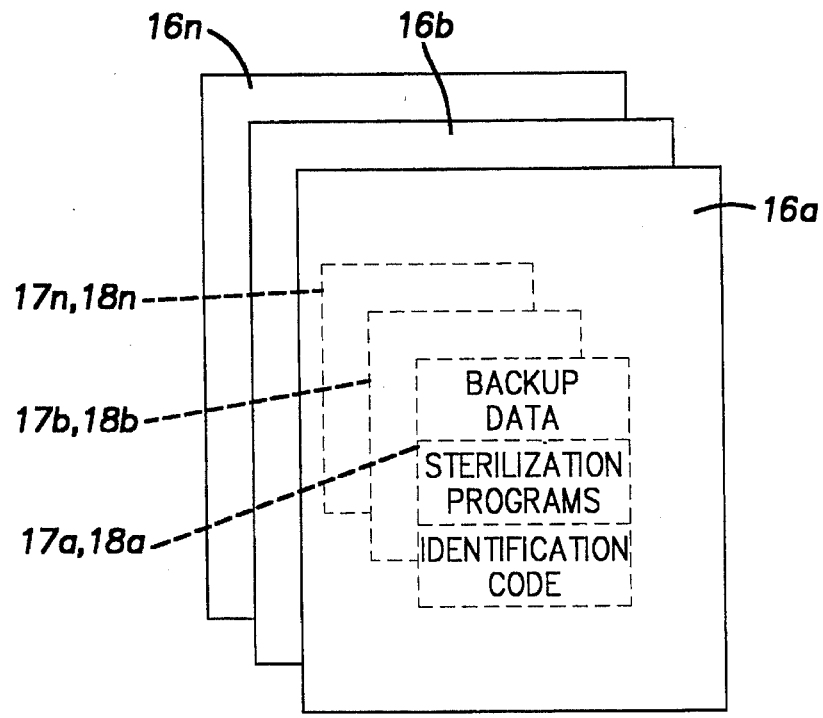
FIG. 4 is a block diagram of a part of the control unit.
Figure 4:
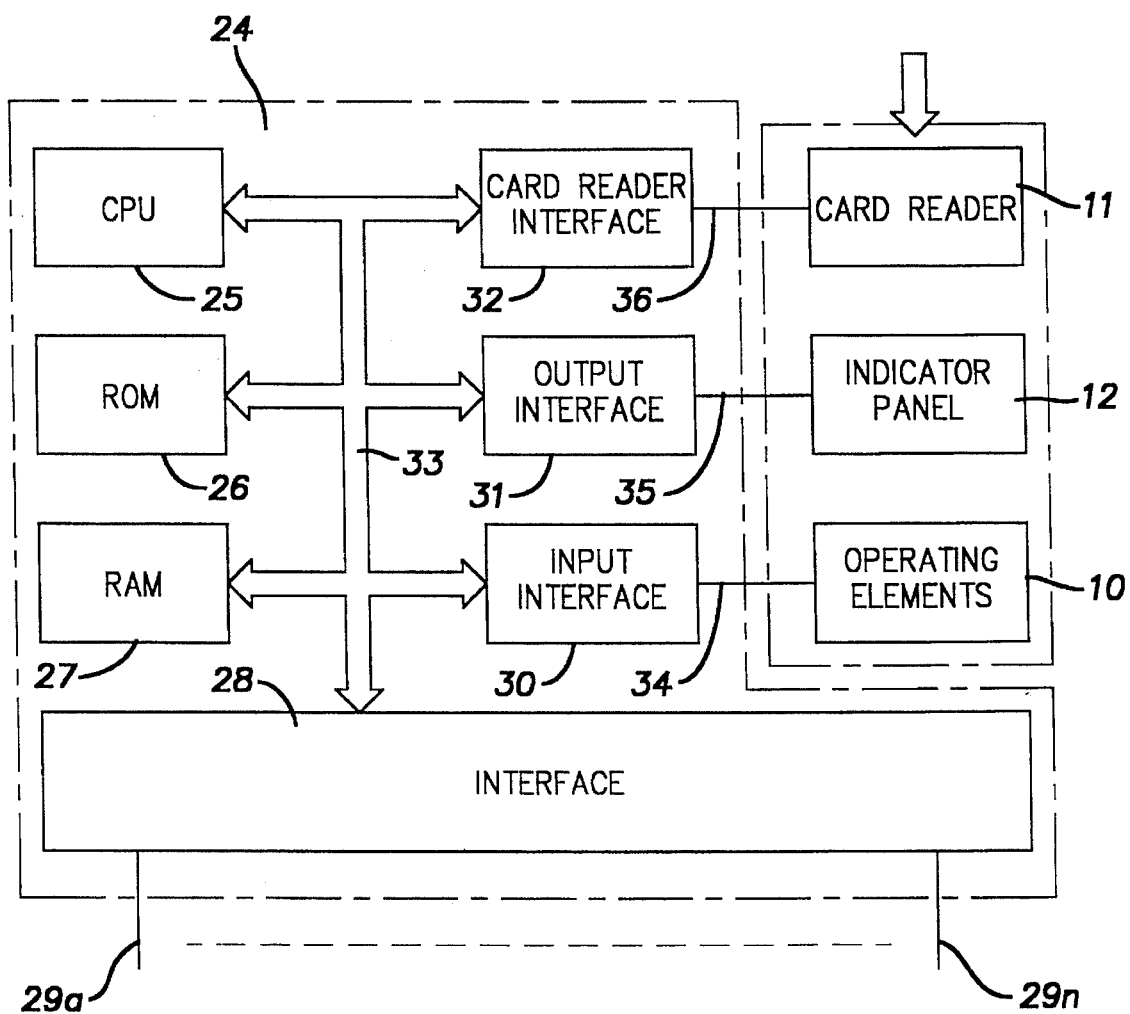

Designated 24 in FIG. 4 is a part of the control unit. It is that part of the control unit with computing means 25, memory means 26, 27 and interface circuits 28, 30, 31 and 32 which are electrically connected to the other electrical parts of the control unit. The memory means 26 and 27 are divided into a ROM 26, in which the program code for operating the computing means is stored, and a RAM 27. Present in the latter is at least one non-volatile battery-buffered area in which configuration data and initialization data as well as identification codes and authorization numbers are stored. Interface 28 contains electric circuits which are connected to other control elements of the control unit via electric lines 29a to 29n. Thus signals are emitted by this interface to control the vaccuum pump, the steam generator, the locking of the door, etc., and control signals are received from the sensors built into the sterilization chamber as well as from other monitoring sensors, and conveyed in a suitable format to the computing means for further processing. The operating elements disposed on the control panel 9 are connected to the input interface 30 via a first electric connecting cable 34. On the output interface the indicator panel 12 is linked to its various displays via a second electric connecting cable 35. The card reader is connected to the card reader interface 32 via a third electric connecting cable 36. Shown as 16a to 16n are a large number of chip cards, each of which can contain in its further memory means 18a–18n of the electronic component 17a–17n data to control, configure and/or operate the autoclave.

Shown as 33 are bus connections with which the aforementioned components 25, 26, 27, 28, 30, 31, and 32 of the part of the control unit designated 24 are connected with each other. As is common practice in microprocessing technology, the bus connections are divided into address bus, data bus and control bus (not shown in the figure).

The functions of the individual chip cards, described at the beginning, especially to block or enable individual operational elements, to block or enable the printer, or to input identification codes or authorization numbers, are carried out with the control buttons 10d and the shift button 11c after insertion of the corresponding chip card into card reader 11.

Figure 5:
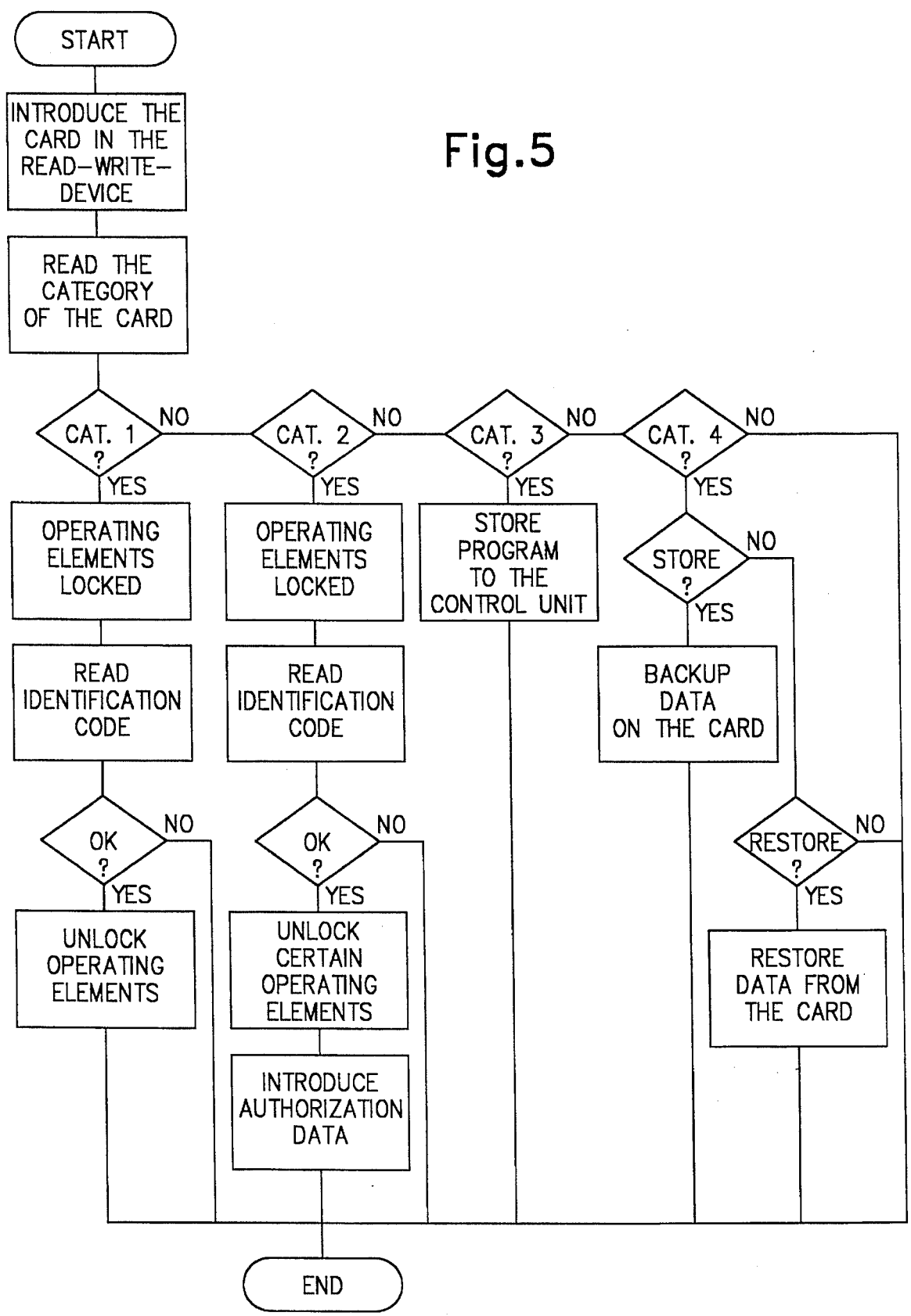
FIG. 5 illustrates a flow diagram of operation for four categories of chip cards.

FIG. 5 illustrates a flow chart of operation for four categories of the chip cards 16a–16n. A first category of the chip cards 16a–16n is intended for operating personnel of the autoclave, a first identification code is contained in the further memory means 18a–18n of these chip cards 16a–16n in such a way that the operating elements 10 are ready to input control signals only after the card reader 11 reads the first identification code and the control unit 6 checks the first identification code. A second category of the chip cards 16a–16n is intended for executive personnel, a second identification code is contained in the further memory means 18a–18n of these chip cards 16a–16n in such a way that, after the card reader 11 reads the second identification code and the control unit 6 checks the second identification code, only selected operating elements 10 are enabled for further use and data can be entered into the control unit 6 to determine who is authorized to operate the autoclave. Output of the authorization data is possible on the indicator panel 12 or the printer 8. A third category of the chip cards 16a–16n is intended to convey special sterilization programs stored in the further memory means 18a–18n of these chip cards 16a–16n to the control unit 6 via the card reader 11. A fourth category of the chip cards 16a–16n is intended to store, in the further memory means 18a–18n of these chip cards 16a–16n, data stored in the memory means 26, 27 of the control unit 6 on the configuration of the autoclave. The fourth category of the chip cards 16a–16n is additionally intended to convey data stored in the further memory means 18a–18n of these chip card 16a–16n, for a configuration of the autoclave, to the memory means 26, 27 of the control unit 6.

Instead of the card reader and the chip cards described here, it is of course possible to use other devices for reading in and reading out data if these are easy to handle and are good value for money.

I claim:

1. An autoclave, especially for articles used in medical treatment, comprising:

a sterilization chamber for treating articles according to a particular sterilization program;

a control unit to control and monitor various sterilization programs;

operating elements to input control signals to the control unit;

an indicator panel to guide a user and to display working conditions of the autoclave;

a computing means and a memory means each contained in the control unit;

a device for reading data intended for the control unit from a plurality external data carrier elements and writing data received from the control unit to said plurality of external data carrier elements, said device being electrically connectable to said data carrier elements and accessible from outside the autoclave;

a further memory means on each of said external data carrier elements having a non-volatile memory on which data to be read is stored and data to be written is storable; and wherein each of said external data carrier elements is associated with a category of data carrier element and, depending on the category, enables using selected operating elements, starting and executing sterilization programs, or backing-up or restoring data.

2. The autoclave of claim 1, wherein the read-write device is a card reader and the external data carrier elements are chip cards which can be inserted into the card reader and can be electrically connected to the latter, and wherein the card reader is electrically connected to the control unit to exchange data between the control unit and a chip card inserted into the card reader.

3. The autoclave of claim 1, wherein different data is stored in the further memory means depending on the category of data carrier element.

4. The autoclave of claim 1, wherein a first category of the plurality external data carrier elements is intended for operating personnel of the autoclave, a first identification code being contained in the further memory means of said first category of the external data carrier elements such that the operating elements are ready to input control signals only after the reading of the first identification code by the read-write device and the checking thereof in the control unit.

5. The autoclave of claim 1, wherein a third category of the external data carrier elements conveys special sterilization programs stored in the further memory means said third category of external data carrier elements to the control unit via the read-write device.

6. The autoclave of claim 1, wherein a second category of the external data carrier elements is intended for executive personnel, a second identification code being contained in the further memory means of said second category of the external data carrier elements such that after the reading of the second identification code by the read-write device and the checking thereof by the control unit only selected operating elements are enabled for further use and data is enterable into the control unit to determine who is authorized to operate the autoclave.

7. The autoclave of claim 6, wherein authorization data can be output on the indicator panel or on a printer.

8. The autoclave of claim 1, wherein a fourth category of the plurality of external data carrier elements receives data stored in the memory means of the control unit on a configuration of the autoclave for storage in the further memory means of the fourth category of external data carrier elements.

9. The autoclave of claim 8, wherein the fourth category of the external data carrier elements also conveys data stored in the further memory means of the fourth category of the external data carrier elements for a configuration of the autoclave to the memory means of the control unit.

* * * * *